United States Patent
Chen et al.

(10) Patent No.: US 7,432,406 B1
(45) Date of Patent: Oct. 7, 2008

(54) DEHYDROGENATION PROCESS USING A NOBLE METAL ON A TIN CONTAINING ZEOLITE CATALYST

(75) Inventors: John Q. Chen, Glenview, IL (US); Jaime G. Moscoso, Mount Prospect, IL (US); Jeffery C. Bricker, Buffalo Grove, IL (US); Michelle J. Cohn, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 564 days.

(21) Appl. No.: 10/865,271

(22) Filed: Jun. 10, 2004

Related U.S. Application Data

(60) Continuation-in-part of application No. 10/300,193, filed on Nov. 20, 2002, now abandoned, which is a continuation-in-part of application No. 09/693,250, filed on Oct. 20, 2000, now abandoned, which is a division of application No. 09/318,328, filed on May 25, 1999, now abandoned.

(51) Int. Cl.
*C07C 5/327* (2006.01)
(52) U.S. Cl. ...................... 585/654; 585/660
(58) Field of Classification Search ........ 585/651, 585/654, 660, 661, 627, 623; 208/134, 135, 208/136
See application file for complete search history.

(56) References Cited

U.S. PATENT DOCUMENTS

| | | | |
|---|---|---|---|
| 2,620,314 A | 12/1952 | Hoeskstra | 252/448 |
| 4,104,320 A | 8/1978 | Bernard et al. | 260/673.5 |
| 4,447,653 A | 5/1984 | Vora | 568/697 |
| 4,868,342 A | 9/1989 | Verson | 568/697 |
| 4,933,161 A | 6/1990 | Vaughan et al. | 423/328 |
| 4,982,047 A | 1/1991 | Barri et al. | 585/660 |
| 4,990,710 A * | 2/1991 | Dessau et al. | 585/277 |
| 5,122,489 A | 6/1992 | Dessau | 502/66 |
| 5,399,336 A | 3/1995 | Guth et al. | 423/705 |
| 5,518,708 A * | 5/1996 | Skeels et al. | 423/713 |
| 5,736,478 A | 4/1998 | Cortright et al. | 502/74 |
| 5,968,473 A | 10/1999 | Valencia et al. | 423/702 |
| 5,994,606 A | 11/1999 | Iwakura et al. | 585/660 |
| 6,074,624 A | 6/2000 | Nemeth et al. | 423/702 |
| 6,306,364 B1 | 10/2001 | Valencia et al. | 423/713 |
| 6,600,082 B2 | 7/2003 | Le Peltier et al. | 585/434 |
| 2002/0045787 A1 * | 4/2002 | Le Peltier et al. | 585/434 |

OTHER PUBLICATIONS

Huang et al., J. Catal., 159, 340-352, (1996).*

* cited by examiner

*Primary Examiner*—Walter D. Griffin
*Assistant Examiner*—Frank C Campanell
(74) *Attorney, Agent, or Firm*—Frank S Molinaro

(57) ABSTRACT

A dehydrogenation process using an improved noble metal containing catalyst is disclosed. The catalyst comprises a non-acidic molecular sieve having a three-dimensional microporous framework structure of tin, aluminum and silicon tetrahedral oxide units. The non-acidic molecular sieve has a noble metal such as platinum dispersed thereon. The molecular sieve is rendered non-acidic by treating it with an alkali or alkaline earth metal. At least 10% of the tin is in a reduced oxidation state.

19 Claims, No Drawings

DEHYDROGENATION PROCESS USING A NOBLE METAL ON A TIN CONTAINING ZEOLITE CATALYST

CROSS-REFERENCE TO RELATED APPLICATIONS

This application is a continuation-in-part of copending application Ser. No. 10/300,193 filed Nov. 20, 2002 which in turn is a continuation-in-part of application Ser. No. 09/693, 250 filed Oct. 20, 2000, now abandoned, which in turn is a division of application Ser. No. 09/318,328 filed May 25, 1999, now abandoned, all of which are hereby incorporated in their entirety by reference.

FIELD OF THE INVENTION

This invention relates to a process for the dehydrogenation of hydrocarbons using a catalyst which comprises a platinum-group metal dispersed on a non-acidic molecular sieve having a three-dimensional microporous framework structure of tin, aluminum and silicon tetrahedral oxide units.

BACKGROUND OF THE INVENTION

It is well-known to use naturally occurring and synthetic crystalline microporous materials as catalysts in various hydrocarbon conversion processes such as dehydrogenation, reforming, alkylation, etc. For example, the dehydrogenation of aliphatic hydrocarbons to the corresponding olefins can be carried out using as the catalyst a zeolite such as ZSM-5 or zeolite-L, on which has been deposited platinum metal.

Specifically, U.S. Pat. No. 4,990,710 discloses a tin containing microporous material on which is also deposited platinum. The material is used to catalyze dehydrogenation and dehydrocyclization of hydrocarbons. U.S. Pat. No. 4,104,320 discloses dehydrocyclizing aliphatic hydrocarbons in the presence of hydrogen and a catalyst consisting essentially of a L-zeolite having an exchangeable alkaline metal such as potassium and at least one metal from Group VIII of the periodic table and tin and germanium. U.S. Pat. No. 5,122, 489 discloses a non-acidic dehydrogenation catalyst comprising a crystalline microporous material which contains a modifier selected from the group consisting of tin, thallium, indium, and lead and a dehydrogenation metal selected from the Group VIII metals of the periodic table. The microporous material has a Si/Al ratio of at least 2 and preferably at least 10.

U.S. Pat. No. 5,736,478 discloses a catalyst for dehydrogenating paraffins which comprises platinum, tin and potassium supported on an L-type zeolite. The catalyst is prepared by first impregnating a potassium L-zeolite with a Group IVA metal, e.g., tin, calcining and then impregnating with a Group VIII metal. U.S. Pat. No. 6,600,082 B2 discloses a PtSn catalyst in which the Sn is in a reduced state. The patentees state that the support can be zeolites such as ZSM-5, but the Sn is not in the zeolite framework. Finally, U.S. Pat. No. 5,518,708 discloses molecular sieves in which some of the aluminum atoms in the framework have been replaced by tin atoms.

The common characteristic of these dehydrogenation catalysts, is that both the dehydrogenation metal, e.g., platinum, and the modifier metal, e.g., tin, are either dispersed on the microporous material or are present "intrazeolitic". By intrazeolitic is meant that the metals are in the channels of the microporous or zeolitic material. In contrast to these catalysts, applicants have developed a novel dehydrogenation catalyst in which the tin modifier metal is present as a tetrahedral oxide unit in the framework of the zeolite or microporous material. Specifically, the catalyst comprises a noble metal such as platinum dispersed on a non-acidic molecular sieve having a three-dimensional microporous framework structure of tin, aluminum and silicon tetrahedral oxide units and having an empirical formula on an anhydrous basis of $mA:(Sn_wAl_xSi_y)O_2$ where A is at least one exchangeable cation, m is the mole fraction of A and w, x and y are the mole fractions of tin, aluminum and silicon respectively. Preferably the molecular sieve has the crystal structure of zeolite-L. Applicants' catalyst is also characterized in that at least a portion of the tin is in a reduced oxidation state and preferably in the zero valent state.

SUMMARY OF THE INVENTION

As stated, the present invention relates to a process for dehydrogenating hydrocarbons. Accordingly, one embodiment of the invention is a process for dehydrogenating a hydrocarbon feedstream comprising contacting the feedstream at dehydrogenation conditions with a dehydrogenation catalyst, to give a dehydrogenation product, the catalyst comprising a noble metal dispersed on a non-acidic molecular sieve having a three-dimensional microporous framework structure of tin, aluminum and silicon tetrahedral oxide units and which has a unit empirical formula on an anhydrous basis of:

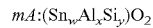

$$mA:(Sn_wAl_xSi_y)O_2$$

where "A" is at least one exchangeable cation, "m" is the mole fraction of A and varies from about 0.01 to about 0.49, "w" is the mole fraction of Sn and varies from about 0.01 to about 0.49, "x" is the mole fraction of Al and varies from about 0.01 to about 0.49 and "y" is the mole fraction of Si and varies from about 0.50 to about 0.98, the molecular sieve characterized in that it has the crystal structure selected from zeolite-L, faujasite, zeolite X, zeolite Y, zeolite beta, ferrierite, MFI and erionite and where at least 10% of the Sn is in a reduced oxidation state.

Another embodiment of the invention is a process for dehydrogenating a hydrocarbon feedstream comprising contacting the feedstream at dehydrogenation conditions with a dehydrogenation catalyst, to give a dehydrogenation product, the catalyst comprising a noble metal dispersed on a non-acidic molecular sieve having a three-dimensional microporous framework structure and which has an empirical formula on an anhydrous basis and in terms of molar oxides of:

$$mA:(Sn_wAl_xSi_y)O_2$$

where "A" is at least one exchangeable cation, "m" is the mole fraction of A and varies from about 0.01 to about 0.49, "w" is the mole fraction of Sn and varies from about 0.01 to about 0.49, "x" is the mole fraction of Al and varies from about 0.01 to about 0.49 and "y" is the mole fraction of Si and varies from about 0.50 to about 0.98, the non-acidic molecular sieve characterized in that it has the crystal structure selected from zeolite-L, faujasite, zeolite X, zeolite Y, zeolite beta, ferrierite, MFI and erionite and where at least 10% of the Sn is in a reduced oxidation state, the non-acidic molecular sieve prepared by the process of:

a) contacting a crystalline microporous alumino-silicate zeolite having a framework structure of aluminum and silicon tetrahedral oxide units, a molar ratio of $SiO_2\backslash Al_2O_3$ of at least two and having the crystal structure of zeolite-L, faujasite, zeolite X, zeolite Y, zeolite beta, ferrierite, MFI and erionite, with a fluoro salt of tin, said fluoro salt being in the form of an aqueous solution or slurry at a pH of about 3 to about 7, and isolating the tin substituted molecular sieve;

b) treating the molecular sieve to render it non-acidic;

c) depositing a noble metal onto the molecular sieve; and d) reducing the noble metal containing molecular sieve at reducing conditions to provide the catalyst.

These and other objects and embodiments will become more apparent after a detailed description of the invention.

DETAILED DESCRIPTION OF THE INVENTION

One essential component of the dehydrogenation catalyst of the present invention is a molecular sieve having a three-dimensional microporous framework structure of tin, aluminum and silicon tetrahedral oxide units. The molecular sieve has an empirical formula on an anhydrous basis of:

$$mA:(Sn_w Al_x Si_y)O_2$$

where "A" is at least one exchangeable cation, "m" is the mole fraction of A and varies from about 0.01 to about 0.49, "w" is the mole fraction of tin and varies from about 0.01 to about 0.49, "x" is the mole fraction of aluminum and varies from about 0.01 to about 0.49 and "y" is the mole fraction of silicon and varies from about 0.50 to about 0.98. The "A" exchangeable cation is selected from the group consisting of the alkali and alkali earth metals. Specific examples include, but are not limited to, sodium, potassium, lithium, rubidium, cesium, barium, magnesium, calcium, and strontium and mixtures thereof. Preferred exchangeable cations are potassium, cesium, barium, sodium and mixtures thereof, with potassium being especially preferred.

The molecular sieves are conveniently prepared by the technique disclosed in U.S. Pat. No. 5,518,708 which teachings are incorporated by reference. Generally, the process involves contacting a crystalline zeolite having a molar $SiO_2/Al_2O_3$ ratio of at least 2 with an effective amount of a fluoro salt of tin, preferably in an amount of at least 0.0075 moles per 100 grams of zeolite starting material, the fluoro salt being in the form of an aqueous solution or slurry which is contacted with the zeolite either incrementally or continuously at a slow rate (optionally in the presence of a buffer) whereby framework aluminum atoms of the zeolite are removed and replaced by tin atoms. The zeolites which can be used as the starting material and thus are part of the catalyst for the present invention include zeolite-L, zeolite-X, zeolite-Y, zeolite-Beta, faujasite, ferrierite, erionite and MFI. MFI is the identifying code of a structure type as defined by the Structure Commission of the International Zeolite Association and published in the "Atlas of Zeolite Structure Types" Meier et al., editors, Elsevier Publisher, Fourth Revised Edition, 1996, pp. 146-147.

The desired zeolite is contacted at effective process conditions with an effective amount of a fluoro salt of tin and then the tin containing molecular sieve product is isolated from the reaction mixture. An effective amount of the fluoro salt is at least 0.0075 moles of the fluoro salt of tin per 100 grams of zeolite starting material with the fluoro salt being in the form of a solution or a slurry. Although the fluoro salt is preferably provided as an aqueous solution or slurry, it is believed that solutions or slurries employing alcohols or other organic solvents can be employed.

It is necessary that the solution or slurry be maintained at an effective pH. The effective pH is a pH such that under effective process conditions; a) monomeric species of the tin is present in the reaction solution; and b) the pH is high enough to avoid undue destructive acidic attack on the particular zeolite structure, apart from the intended reaction with an effective amount of the fluoro salt. The effective amount of fluoro salt is that amount which provides sufficient fluoride and tin for the process and the desired amount of tin in the final molecular sieve product. The effective pH value for this invention is generally greater than one (1), more preferably greater than 3 (three) and most preferably in the range of about 3 to about 7 (seven).

A pH of about 3 or more usually assures that no acid degradation of the zeolite occurs but it may not necessarily be the optimum pH for the formation of monomeric species of tin in the solution. At pH values below about 3, crystal degradation of many zeolites is found to be unduly severe. Whereas at pH values higher than 7, insertion of the tin may be slow from a practical standpoint as a result of the solubility of tin at these pHs and as a result of certain polymerization reactions. A pH of 7 and above typically results in no monomeric species of tin being present in the solution so that very little substitution of this metal atom in the framework would occur. Frequently the polymeric species of tin will precipitate as solid oxides or hydrous oxides at pH 7 or above.

The fluoro salt solution or slurry is brought into contact with the zeolite either incrementally or continuously at a slow rate whereby framework aluminum atoms of the zeolite are removed and replaced by tin atoms from the fluoro salt and which preferably retains at least 80 percent and more preferably at least 90 percent of the crystal structure of the starting zeolite.

The fluoro salt used as the aluminum extractant and also as the source of tin, which is inserted into the zeolite structure in place of the extracted aluminum, can be any of the fluoro salts having the general formula:

$$A_{2/b}SnF_6 \text{ or } A_{2/b}SnF_4$$

where "A" is a metallic or non-metallic cation, having the valence "b". Cations represented by "A" include alkylammonium, $H^+$, $NH_4^+$, $Mg^{++}$, $Li^+$, $Na^+$, $K^+$, $Ba^{++}$, $Cd^{++}$, $Cu^{++}$, $Ca^{++}$, $Cs^+$, $Fe^{++}$, $Co^{++}$, $Pb^{++}$, $Mn^{++}$, $Rb^+$, $Ag^+$, $Sr^{++}$, $Tl^+$ and $Zn^{++}$. The ammonium and hydronium cation forms of the fluoro salt are generally preferred because of their solubility in water and also because these cations form water soluble by-product salts upon reaction with the zeolite, e.g., $(NH_4)_3AlF_6$ and/or $(NH_4)_2AlF_5$. Other salts which may be used include a combination of salts of $SnF_2$ and $3/2(NH_4HF_2)$ or $SnF_4$ and $NH_4HF_2$. Preferred fluoro salts are $NH_4SnF_3$;$SnF_2.3/2(NH_4HF_2)$ and $SnF_4.NH_4HF_2$.

Whether it is necessary or desirable to buffer the reaction system or select a particular fluoro salt concentration to control the pH is readily determined for each zeolite species by routine observation and evaluation. The question of whether the reaction system may advantageously be buffered will in large part depend on the selection of the particular starting zeolite, since zeolites have varying tolerances to acid and base media. For example, some zeolites such as mordenite and clinoptilolite can withstand very low pH conditions and a high level of dealumination without collapse of the crystal structure. When it is advantageous to buffer the reaction mixture in a particular pH range the reaction mixture may be buffered in a manner as generally heretofore employed in the art. The use of buffering salts, such as ammonium acetate, or use of an inert solid to react with excess acid or base, e.g., clays or aluminas, may be suitable to buffer the pH of the reaction mixture.

Theoretically, there is no lower limit for the concentration of fluoro salt of tin in the aqueous solution or slurry employed. A slow rate of addition of the fluoro salt generally provides adequate time for the insertion of tin as a framework substitute for extracted aluminum before excessive aluminum extraction occurs with consequent collapse of the crystal structure. Practical commercial considerations, however, may require that the reaction proceed as rapidly as possible, and accordingly, the conditions of reaction temperature and reagent concentrations will necessarily be optimized with respect to each zeolite starting material and with respect to commercial operation. In general it is believed that the more highly siliceous the zeolite, the higher the permissible reaction temperature and the lower the pH conditions which may be employed in the instant process. In general the preferred effective reaction temperature is within the range between about 10° C. and about 99° C., preferably between about 20° C. and 95° C., but temperatures of 125° C. or higher and as low as 0° C. are believed employable in some instances with some zeolite starting materials and with fluoro salts in a form other than aqueous solutions or slurries. The maximum concentration of fluoro salt in the aqueous solution employed is, of course, interrelated to the temperature and pH factors and also with the time of contact between the zeolite and the solution and the relative proportions of zeolite and fluoro salt. Solutions having fluoro salt concentrations of between about $10^{-3}$ moles per liter of solution and up to saturation of the solution can be employed, but it is preferred that concentrations in the range of between about 0.5 and about 1.0 moles per liter of solution be used. In addition, as herein before discussed, slurries of the fluoro salts of tin may be employed. The aforementioned concentration values are with respect to true solutions, and are not intended to apply to the total fluoro salts in slurries of the salts in water. Even very slightly soluble fluoro salts can be slurried in water and used as a reagent, the undissolved solids being readily available to replace dissolved molecular species consumed in reaction with the zeolite. As stated hereinabove, the amount of dissolved fluoro salts employed with respect to the particular zeolite being treated will depend to some extent upon the physical and chemical properties of the individual zeolites and other effective process conditions. However, the minimum value for the amount of fluoro salt to be added is preferably at least equivalent to the minimum mole fraction of aluminum to be removed from the zeolite.

In specifying the proportions of the zeolite starting materials or adsorption properties of the zeolite product and the like herein, the "anhydrous state" of the zeolite will be intended unless otherwise stated. The term "anhydrous state" is employed herein to refer to a material substantially devoid of both physically adsorbed and chemically adsorbed water. In general a zeolite may be prepared in the anhydrous state by heating the zeolite in dry air at about 450° C. for about 4 hours.

In order to facilitate insertion of the tin into the framework, the original zeolite is usually converted to the ammonium form before treatment with the fluoro salts. Accordingly, the tin containing molecular sieve is now exchanged with the desired alkali or alkali earth metal. This is done by contacting the tin containing molecular sieve, e.g., zeolite L, with an aqueous solution of the desired alkali or alkaline earth metal compound, e.g., KCl. The solution is contacted with the molecular sieve at a temperature of about 50° C. to about 98° C. for a time of about 0.5 to about 2 hours, filtered and washed with water. This procedure is repeated several times (3 to 6) to obtain the desired degree of exchange of the metal. In a preferred embodiment substantially all of the acid sites are occupied by an alkali or alkaline earth metal, thereby rendering the molecular sieve "non-acidic". In terms of ion exchanging, the procedure is carried out until substantially all the acid sites are occupied by alkali or alkaline earth metal cations. An especially preferred non-acidic molecular sieve is a potassium form on the molecular sieve and particularly potassium L-zeolite. After exchanging with the desired metal cation, the molecular sieve is dried as described above.

Having obtained the desired tin-containing molecular sieve, it can now be impregnated or exchanged with a noble metal compound or mixed with a binder, formed into a desired shape and then impregnated or exchanged with a noble metal compound, although not necessarily with equivalent results. The noble metals which can be used in the catalyst of this invention are platinum, palladium, rhodium, ruthenium, osmium, iridium and mixtures thereof, with platinum being preferred. Illustrative of the noble metal compounds which can be used are $Pt(NH_3)_4Cl_2$, $Pt(NH_3)_4(OH)_2$, $Pt(NH_3)_4(NO_3)_2$, $Pt(acac)_2$, chloroplatinic acid, rhodium trichloride, hexa-amminerhodium chloride, rhodium carbonylchloride, sodium hexanitrorhodate, chloropalladic acid, palladium chloride, palladium nitrate, diamminepalladium hydroxide, tetraamminepalladium chloride, hexachloroiridate (IV) acid, hexachloroiridate (III) acid, ammonium hexachloroiridate (III), ammonium aquohexachloroiridate (IV), ruthenium tetrachloride, hexachlororuthenate, hexaammineruthenium chloride, osmium trichloride and ammonium osmium chloride.

Whether the noble metal is deposited onto the molecular sieve before or after the molecular sieve is combined with a binder and formed into a desired shape, the procedure is the same. Typically, an aqueous solution containing the desired noble metal compound is added to the molecular sieve, the impregnated molecular sieve is dried at a temperature of about 90° C. to about 150° C. for a time of about 8 to about 24 hours and then calcined at a temperature of about 350° C. to about 550° C. for a time of about 1 to about 4 hours. The noble metal content is typically from about 0.01 to about 5 wt. % and preferably from about 0.05 to about 2 wt. %.

When the catalyst of the invention is used in a dehydrogenation process, it is reduced so that the platinum is substantially in the zerovalent state. Although this reduction will take place during the initial time period of operation, it is preferred to reduce the catalyst prior to the start of the dehydrogenation process. Reduction is usually carried out in situ, i.e. in the reactor used for the dehydrogenation process, using a reducing agent such as pure hydrogen and preferably dry hydrogen (less than 20 vol. ppm water). The reducing agent is contacted with the catalyst at reducing conditions which include a temperature from about 200° C. to about 650° C. for a time of about 0.5 to about 10 hours which is effective to reduce substantially all of the platinum.

The reduced catalyst has been analyzed by Mossbauer spectroscopy which examines the local electronic structure of the tin (oxidation state, environment, chemical bonding). Using this characterization tool, it has been found that the catalysts of the invention are characterized in that at least 10% and preferably at least 15% of the tin present in the catalyst is in a reduced state. By reduced state is meant $Sn^0$. The Mössbauer analysis indicated that the reduced Sn is associated with the Pt; meaning that there is significant bonding between those Sn and Pt atoms.

If it is desired to combine the tin containing molecular sieve with a matrix or binder material, this can be done by means well known in the art. The final catalyst composition can contain from about 5 to about 50 wt. % of the total weight as binder. Materials which can be used as binders include without limitation silica, alumina, magnesia, titania, aluminum phosphate, zirconia, zinc oxide, clays and mixtures thereof. Of these, it is preferred to use a non-acidic binder such as but not limited to silica, magnesia, zirconia, zinc oxide, aluminum phosphate and mixtures thereof. The binder and tin containing molecular sieves are combined along with water and a gelling or peptizing agent such as ammonium acetate and then milled for a time of about 0.1 to about 2 hours. Extrusion aids such as methocel can also be added. The resultant mixture is next formed into any desired shapes such as spheres, extrudates, rods, pills, pellets, tablets or granules. For example, extrudates can be formed by taking the above mixture and extruding it through a die, e.g., a $\frac{1}{16}$" die, dried and then calcined at a temperature of about 350° C. to about 550° C. for a time of about 1 to about 3 hours.

Spherical shapes can be made by the well known oil-drop method which is disclosed in U.S. Pat. No. 2,620,314 which is incorporated by reference. The oil drop method comprises forming an aluminum hydrosol by any of the techniques taught in the art and preferably by reacting aluminum metal with hydrochloric acid; combining the hydrosol with the molecular sieve and a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged gel spheres are then washed and dried at a relatively low temperature of about 80° C. to about 150° C. then calcined at a temperature of about 455° C. to 705° C. for a period of about 1 to about 20 hours. This treatment effects conversion of the hydrogel to the corresponding crystalline gamma-alumina. Silica sols (or other sols) can be used in this procedure to provide a non-acidic binder.

The catalysts of the instant invention are useful as dehydrogenation catalysts in which a dehydrogenatable hydrocarbon is contacted with the catalyst at dehydrogenation conditions to yield a dehydrogenated hydrocarbon, e.g., olefins. The hydrocarbons which can be dehydrogenated according to the present invention include those having from 2 to 30 number of carbon atoms. Dehydrogenation is usually carried out in a dehydrogenation zone which are well known in the art as exemplified by U.S. Pat. No. 4,447,653 and U.S. Pat. No. 4,868,342 both of which are incorporated by reference in their entirety. The precise dehydrogenation temperature and pressure employed in the dehydrogenation zone will depend on a variety of factors, such as the composition of the hydrocarbon feedstock, the activity of the selected catalyst and the hydrocarbon conversion rate. Preferred conditions include a temperature of about 350° C. to about 700° C., a pressure of about 50 kPa to about 1,500 kPa, a $H_2$:hydrocarbon mole ratio of about 0.1:1 to about 10:1 and a space velocity of about 0.1 to about 100 $hr^{-1}$.

In order to more fully illustrate the instant invention, the following examples are set forth. It is to be understood that the examples are only by way of illustration and are not intended as an undue limitation on the broad scope of the invention as set forth in the appended claims.

EXAMPLE 1

A zeolite L (potassium form) was obtained from Tosoh Corp. and was exchanged with $NH_4^+$ ions by first mixing 220 g of the zeolite L with 1600 g of deionized water, heating the mixture with stirring to 75° C. at which point about 3 moles of $NH_4Cl$ were added and the mixture stirred for about 1.5 hours. The mixture was filtered, washed with water and the exchange procedure repeated 4 to 5 times. Elemental analysis showed that the potassium content was reduced from 13.8 wt. % to 3.7 wt. %.

In a container, 200 g of the above $NH_4$ zeolite L were mixed with 1600 g of deionized water and heated to 75° C. with stirring. To this there was added 100 ml of an aqueous solution containing 0.0134 moles of $SnF_4$ and 0.112 moles of $NH_4HF_2$. This solution was added in 10 ml aliquots over a ten minute period. The resultant mixture was digested for 1 hour, filtered and washed with water. Elemental analysis showed the molecular sieve contained 0.7 wt. % tin.

The $NH_4$—Sn-zeolite-L molecular sieve was now exchanged with potassium as described above for the ammonium exchange except that a solution of KCl was used. Elemental analysis showed that the molecular sieve now contained 14 wt. % potassium.

EXAMPLE 2

Platinum was deposited onto the Sn—K-zeolite-L molecular sieve of example 1 as follows. A 10 g sample of the Sn—K-zeolite-L molecular sieve was calcined at 550° C. for 2 hours. The calcined molecular sieve was placed in a container to which there were added 50 mg of tetramine platinum chloride ($Pt(NH_3)_4Cl_2$) dissolved in 6 g of water. Addition was carried out dropwise. The impregnated support was dried at 150° C. for 16 hours. Elemental analysis showed that the catalyst contained 0.3 wt. % platinum. This sample was designated sample A.

EXAMPLE 3

An extruded Sn—K-zeolite-L molecular sieve was prepared by mixing 144 g of a Sn—K-zeolite-L molecular sieve prepared as in example 1 with 11.3 g of Cabosil silica and a solution of 57 g of colloidal silica (LUDOX®-AS-40) plus 30 g of water and 6 g of ammonium acetate. The resultant mixture was mixed for one hour. Next 5 g of methocel along with 41 g of water were added and the mixture mixed for an additional 40 minutes. The resultant mixture was extruded through a $\frac{1}{16}$ inch die and the extrudates were then dried at 98° C. overnight and then calcined at 550° C. for 3 hours. Finally the extrudates were washed with KCl to eliminate any acidity as a result of the extrusion process.

These extrudates were impregnated with platinum as in example 2 to give a catalyst with a platinum content of 0.25 wt. %. This catalyst was identified as sample B.

EXAMPLE 4

In a rotary evaporator 6 grams of a zeolite L (potassium form) obtained from Tosoh Corp. were impregnated with a solution of 110 mg. of $SnCl_4.5H_2O$ dissolved in 30 grams of water and having added to it 0.49 grams of HCl. The mixture was rotated at room temperature for 1 hour and then dried for 2 hours. The dried product was calcined at 550° C. for 2 hours.

The above product was now impregnated with 35 mg. of tetramine platinum chloride in sufficient water using the incipient wetness technique and then dried at 150° C. for 16 hours. Elemental analysis showed that the catalyst contained 0.3 wt. % platinum and 0.6 wt. % tin. This sample was designated sample C.

EXAMPLE 5

Samples B and C were tested for the dehydrogenation of isobutane as follows. In a reactor there were loaded 210 mg.

of the desired catalyst having a particle diameter of 40-60 mesh. The catalyst was reduced in situ by heating the reactor under hydrogen to a temperature of 645° C. for 10 minutes, then ramping the temperature to 655° C. and holding it there for 2 hours. The reactor temperature was then lowered to 600° C. and isobutane and hydrogen were flowed over the catalyst at a H$_2$/hydrocarbon mole ratio of 0.2 at a Weight Hourly Space Velocity (WHSV) of 17 hr$^{-1}$ with the addition of 6000 ppm of water. Conversion and Selectivity to isobutene were calculated as a function of time on stream. The results after 20 hours on stream are presented below.

| Effect of Sn Placement on Catalyst Performance* | | |
|---|---|---|
| Catalyst I.D. | Conversion (%) | Selectivity (%)[1] |
| B | 57 | 97.9 |
| C | 41 | 95.5 |

*Performance after 20 hours on stream.
[1] Selectivity to isobutene

The results clearly indicate that the catalyst of the invention (catalyst B) has much better conversion and much better selectivity. When selectivities are this high, one must look at the residual amount, i.e., the amount not converted to isobutene. Here the residual amount for catalyst C is 4.5% versus 2.1% for catalyst B. Thus catalyst C has 53% more non-isobutene product than catalyst B. Catalyst B is, therefore, clearly superior.

EXAMPLE 6

In a container 200 g of ammonium-exchanged zeolite L was slurried in distilled water and heated to 75° C. A solution containing 2.2 g SnF$_4$ and 6.5 g NH$_4$HF$_2$ in 150 g of distilled water was added incrementally over a period of 10 minutes to the zeolite. Following the addition of the tin solution, the slurry was reacted at 75° C. for 1.5 hrs. The product was filtered and washed free of soluble fluoride. The solid product was white and showed the characteristic crystal structure of zeolite L as indicated by X-ray powder diffraction.

In a container 30 g of NH$_4$—Sn-zeolite L solid was slurried in distilled water, and the slurry was stirred and heated to 75° C. Then 50 g KCl was added and the mixture was allowed to react for about 1½ hours, filtered, and the solid was washed with deionized water. This procedure was repeated five times to yield K—Sn-zeolite L. This sample was analyzed and found to have 0.57% Sn, 9.38% Al, 30.2% Si, 13.7% K, LOI=10.8%. The K—Sn—L was calcined at 550° C. for 2 hrs and then 5 g were reduced with hydrogen for 2 hours at 650° C. The reduced sample was analyzed by Mossbauer spectroscopy and determined to have only tin oxide, i.e. Sn$^{+4}$.

An 8 g sample of the calcined K—Sn—L from above was impregnated (evaporative impregnation) with a solution containing 43 mg of tetraamineplatinum chloride. After impregnation the platinum containing zeolite was calcined at 200° C. for ±2 hour and then at 350° C. for 2 hours and then reduced with hydrogen at 650° C. for 2 hours. Chemical analysis of this sample showed that it contained 0.39 wt. % Pt and 0.57 wt. % Sn. This sample was also analyzed by Mossbauer spectroscopy which showed that 17% of the Sn was in the Sn$^0$ reduced state and that there was significant bonding between the reduced Sn atoms and the Pt atoms.

What is claimed is:
1. A process for dehydrogenating a hydrocarbon feedstream comprising contacting the feedstream at dehydrogenation conditions with a dehydrogenation catalyst, to give a dehydrogenation product, the catalyst comprising a noble metal dispersed on a non-acidic molecular sieve having a three-dimensional microporous framework structure of tin, aluminum and silicon tetrahedral oxide units and which has a unit empirical formula on an anhydrous basis of:

$$mA:(Sn_wAl_xSi_y)O_2$$

where "A" is at least one exchangeable cation, "m" is the mole fraction of A and varies from about 0.01 to about 0.49, "w" is the mole fraction of Sn and varies from about 0.01 to about 0.49, "x" is the mole fraction of Al and varies from about 0.01 to about 0.49 and "y" is the mole fraction of Si and varies from about 0.50 to about 0.98, the molecular sieve characterized in that it has the crystal structure selected from zeolite-L, faujasite, zeolite X, zeolite Y, zeolite beta, ferrierite, MFI and erionite and where at least 10% of the Sn is in a reduced oxidation state.

2. The process of claim 1 where the dehydrogenation conditions include a temperature of about 350° C. to about 700° C., a pressure of about 50 kPa to about 1,500 kPa, a H$_2$:hydrocarbon ratio of about 0.1:1 to about 10:1 and a space velocity of about 0.1 to about 100 hr$^{-1}$.

3. The process of claim 1 where "A" is selected from the group consisting of alkali and alkaline earth metals.

4. The process of claim 3 where the alkali metal is potassium.

5. The process of claim 1 where the molecular sieve has the crystal structure of zeolite-L.

6. The process of claim 1 where the noble metal is platinum and is present in a concentration of about 0.05 to about 2.

7. The process of claim 1 where the catalyst further comprises a non-acidic binder and comprises a shaped article having a shape selected from the group consisting of extrudates, pellets, pills and spheres.

8. The process of claim 7 where the non-acidic binder is selected from the group consisting of silica, zirconia, magnesia, zinc oxide, aluminum phosphate and mixtures thereof and is present from about 5 to about 50 wt. % of the finished catalyst.

9. The process of claim 7 where the catalyst is in the shape of extrudates.

10. The process of claim 1 where the reduced oxidation state of the tin is the zero valent state.

11. A process for dehydrogenating a hydrocarbon feedstream comprising contacting the feedstream at dehydrogenation conditions with a dehydrogenation catalyst, to give a dehydrogenation product, the catalyst comprising a noble metal dispersed on a molecular sieve having a three-dimensional microporous framework structure and which has an empirical formula on an anhydrous basis and in terms of molar oxides of:

$$mA:(Sn_wAl_xSi_y)O_2$$

where "A" is at least one exchangeable cation, "m" is the mole fraction of A and varies from about 0.01 to about 0.49, "w" is the mole fraction of Sn and varies from about 0.01 to about 0.49, "x" is the mole fraction of Al and varies from about 0.01 to about 0.49 and "y" is the mole fraction of Si and varies from about 0.50 to about 0.98, the molecular sieve characterized in that it has the crystal structure selected from zeolite-L, faujasite, zeolite X, zeolite Y, zeolite beta, ferrierite, MFI and erionite and where at least 10% of the Sn is in a reduced oxidation state, the catalyst prepared by the process of:
a) contacting a crystalline microporous alumino-silicate zeolite having a framework structure of aluminum and silicon tetrahedral oxide units, a molar ratio of SiO$_2$ \Al$_2$O$_3$ of at least two and having the crystal structure of zeolite-L, faujasite, zeolite X, zeolite Y, zeolite beta, ferrierite, MFI and erionite, with a fluoro salt of tin, said fluoro salt being in the form of an aqueous solution or slurry at a pH of about 3 to about 7, to provide a tin substituted molecular sieve and isolating the tin substituted molecular sieve;

b) treating the molecular sieve to render it non-acidic;

c) depositing a noble metal onto the molecular sieve; and d) reducing the noble metal containing molecular sieve at reducing conditions to provide the catalyst.

12. The process of claim 11 where the dehydrogenation conditions include a temperature of about 350° C. to about 700° C., a pressure of about 50 kPa to about 1,500 kPa, a H$_2$:hydrocarbon ratio of about 0.1:1 to about 10:1 and a space velocity of about 0.1 to about 100 hr$^{-1}$.

13. The process of claim 11 where "A" is selected from the group consisting of alkali and alkaline earth metals.

14. The process of claim 13 where the alkali metal is potassium.

15. The process of claim 11 where the molecular sieve has the crystal structure of zeolite-L.

16. The process of claim 11 where the noble metal is platinum and is present in a concentration of about 0.01 to about 5 wt. %.

17. The process of claim 11 further comprising in that the catalyst is admixed with a non-acidic binder and formed into a shape selected from the group consisting of extrudates, pellets, pills and spheres.

18. The process of claim 17 where the non-acidic binder is selected from the group consisting of silica, zirconia, magnesia, zinc oxide, aluminum phosphate and mixtures thereof and is present from about 5 to about 50 wt. % of the finished catalyst.

19. The process of claim 17 where the catalyst is in the shape of extrudates.

* * * * *